US00PP15484P2

(12) United States Plant Patent
Olesen et al.

(10) Patent No.: US PP15,484 P2
(45) Date of Patent: Jan. 25, 2005

(54) ROSE PLANT NAMED 'POULCS004'

(50) Latin Name: *Rosa hybrida*
Varietal Denomination: POULcs004

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 107 days.

(21) Appl. No.: 10/341,898

(22) Filed: Jan. 13, 2003

(51) Int. Cl.[7] ..... A01H 5/00
(52) U.S. Cl. ..... Plt./144
(58) Field of Search ..... Plt./144

(56) References Cited

U.S. PATENT DOCUMENTS

PP10,730 P * 12/1998 Olesen et al. ..... Plt./145

OTHER PUBLICATIONS

UPOV ROM GTITM Computer Database, GTI JOUVE Retrieval Software 2003/01 citation(s) for 'POULcs004'.*
http://www.helpmefind.com/rose/pl.php?n=35688.*

* cited by examiner

*Primary Examiner*—Bruce R. Campell
*Assistant Examiner*—W C Haas

(57) ABSTRACT

A new Floribunda garden rose plant which has abundant, white flowers and attractive foliage. This new and distinct variety has shown to be uniform and stable in the resulting generations from asexual propagation.

1 Drawing Sheet

Classification:
Botanical: *Rosa hybrida.*
Variety denomination: 'POULcs004'.
Commercial: Floribunda.

SUMMARY OF THE INVENTION

The present invention constitutes a new and distinct variety of garden rose plant which originated from a controlled crossing between 'POULcape', described and illustrated in U.S. Plant Pat. No. 10,730 issued on Dec. 22, 1998 and 'POULsnows', described and illustrated in U.S. Plant patent application Ser. No. 10/222,212 dated Aug. 16, 2002. The two parents were crossed during the summer of 1994 and the resulting seeds were planted in a controlled environment in Fredensborg, Denmark. The new variety is named 'POULcs004'.

The new variety may be distinguished from its seed parent, 'POULcape' by the following combination of characteristics:

1. 'POULcape' has a bloom diameter of 55 to 65 mm, while 'POULcs004' has a bloom diameter of 70 mm.
2. 'POULcape' has a general tonality of Yellow Group 4D and Yellow Group 10D, while that of 'POULcs004' is White Group 155B.
3. 'POULcape' has a thorn color of Yellow-Green-Group 145D, while that of 'POULcs004' is Greyed-Green Group 196B.

The new variety may be distinguished from its pollen parent, 'POULsnows' by the following combination of characteristics:

1. 'POULsnows' has a bloom diameter of 45 mm, while that of 'POULcs004' is 70 mm.
2. 'POULsnows' has a bud color of Green-White Group 157C, while that of 'POULcs004' is White Group 155B.

The objective of the hybridization of this rose variety was to create a new and distinct variety for garden use with unique qualities, such as:

1. Uniform and abundant flowers;
2. Vigorous, but compact growth when propagated both as a budded rose and on its own roots;
3. Disease resistance.

This combination of qualities is not present in previously available commercial cultivars of this type and distinguish 'POULcs004' from all other varieties of which we are aware.

As part of their rose development program, L. Pernille Olesen and Mogens N. Olesen germinated the seeds from the aforementioned hybridization during winter 1994 and conducted evaluations on the resulting seedlings in a controlled environment in Fredensborg, Denmark.

'POULcs004' was selected in the spring 1995 by the inventors as a single plant from the progeny of the aforementioned hybridization.

Asexual reproduction of 'POULcs004' by traditional budding and rooted cuttings was first done by L. Pernille and Mogens N. Olesen in their nursery in Fredensborg, Denmark in August, 1995. This initial and other subsequent asexual propagations conducted in controlled environments have demonstrated that the characteristics of 'POULcs004' are true to type and are transmitted from one generation to the next.

BRIEF DESCRIPTION OF THE DRAWING

The accompanying color illustration shows as true as is reasonably possible to obtain in color photographs of this type, the typical characteristic of the buds, flowers, leaves, and stems, of 'POULcs004'. Specifically illustrated in the first drawing:

1. Stem showing branching and the attachment of leaves, buds, and peduncles;
2. Flower bud, partially opened bud, and open bloom;
3. Flower petals, detached;
4. Sepals, receptacle, and pedicel;
5. Stem as well as a bare stem exhibiting thorns;
6. Leaves.

DETAILED DESCRIPTION OF THE VARIETY

The following is a description of 'POULcs004', as observed in its growth as a budded plant, grown in a field nursery in Jackson County, Oreg. The plants observed are 3 years old. Color references are made using The Royal Horticultural Society (London, England) Colour Chart, 1995, except where common terms of color are used.

For a comparison, several physical characteristics of the rose variety 'POULsnows', a rose variety from the same inventors described and illustrated in U.S. Plant Patent application Ser. No. 10/222,212 and issued on Aug. 16, 2002, is compared to 'POULcs004' in Chart 1.

CHART 1

| | 'POULcs004' | 'POULsnows' |
|---|---|---|
| Bloom diameter | 70 mm | 45 mm |
| Bud Color | Green-White Group 157C | White Group 155B |
| Pollen color | Yellow-Orange Group 15A | Orange Group 27A |

Parents:
*Seed parent.*—'POULcape'.
*Pollen parent.*—'POULsnows'.

FLOWER AND FLOWER BUD

Blooming habit: Recurrent.
Flower bud:
*Size.*—Upon opening, 25 mm in length from base of receptacle to end of bud.
*Bud diameter.*—18 mm.
*Bud shape.*—Broad based ovoid.
*Bud form.*—Long.
*Bud color.*—As sepals unfold, upper surface of petals is White Group 155B; lower surface is White Group 155B. At ¼ opening, upper surface of Petals is White Group 155B; lower surface is White Group 155B.
*Sepals.*—Color: Upper surface: Yellow-Green Group 145C with Grey-Red Group 180C. Lower surface: Yellow-Green Group 144A with Grey-Red Group 181B. Margins: Enitire. Weak to no foliaceous appendages on three of the five sepals. Surfaces of sepals moderately pubescent. Stipitate glands are present along the margins of the sepals. Shape: Overall sepal shape is lanceolate. Apex is caudate. Base is flat at union with receptacle. Size: 21 mm long×8 mm wide.
*Receptacle.*—Surface: Smooth. Shape: Funnel shaped. Size: Small. 5 mm (h)×9 mm (w). Color: Green Group 144A to 144B.
*Peduncle.*—Surface: Smooth. Length: 30 to 40 mm average length. Diameter: Typical: 3 mm. Observed: 3 mm. Color: Green Group 144A. Strength: Strong.
*Borne.*—Multiples of 3 to 5 flower buds per stem.
*Anthocyanin.*—Color: Grey Red Group 179B.
Flower bloom:
*Fragrance.*—Light and fresh.
*Duration.*—The blooms have a duration on the plant for approximately 7 to 10 days. Petals fall cleanly away from plant.
*Size.*—Average flower diameter is 70 mm when open. Flower depth is 23 mm.
*Form.*—Shape of flower when viewed from the side: Upon opening, upper part: Flattened convex. Upon opening, lower part: Concave. Open flower, upper part: Flattened convex. Open flower, lower part: Concave.
Petalage: Very double. Average range: 55 to 60 petals under normal conditions with 10 to 15 petaloids.
Color:
*Upon opening, petals.*—Outermost petals: Outer side: White Group 155B. Inner Side: White Group 155B. Innermost petals: Outer side: White Group 155B. Inner Side: White Group 155B.
*Upon opening, basal petal spots.*—Outermost petals: Outer side: White Group 155B. Inner Side: White Group 155B. Innermost petals: Outer side: White Group 155B. Inner Side: White Group 155B.
*After opening, petals.*—Outermost petals: Outer side: White Group 155B. Inner Side: White Group 155B. Innermost petals: Outer side: White Group 155B. Inner Side: White Group 155B.
*After opening, basal petal spots.*—Outermost petals: No distinctive coloration at petal base observed. Innermost petals: No distinctive coloration at petal base observed.
General tonality: On open flower White Group 155B. No change at all in the general tonality at the end of the 3rd day. Afterwards, general tonality is White Group 155B.
Petals:
*Petal reflex.*—Somewhat reflexed.
*Petal edge.*—Entire.
*Shape.*—32 mm (l)×25 mm (w).
*Shape.*—Obovate shaped.
*Petaloids.*—Present. Quantity: 10 to 15. Size: 7 mm (w)×8 mm (l). Shape: Round. Color: White Group 155B.
*Thickness.*—Average.
*Arrangement.*—Not Formal.
Reproductive organs:
*Pistils.*—Length: 6 to 7 mm long. Quantity: 30. Color: Yellow-Green Group 145D.
*Pollen.*—Color: Orange-Yellow Group 15A. Quantity: Average.
*Anthers.*—Size: 2 mm long. Color: Gray-Green Group 196D. Quantity: 33 (actual count).
*Filaments.*—Color: Yellow Group 1A. Length: 8 to 10 mm.
*Stigmas.*—Slightly inferior in relation to anthers. Color: Greyed-Green Group 196D.
*Styles.*—Color: Yellow-Green Group 145B to 145C.
*Hips.*—None observed.

PLANT

Plant growth: Moderate, upright to bushy. When grown as a budded field grown plant on *Rosa multiflora* understock, the average height of the plant is 60 to 100 cm and the average width is 60 cm.
Stems:
*Size.*—6 mm diameter×60 cm length.
*Internodal distance.*—50 mm.
*Color.*—Young wood: Green Group 144B. Older wood: Green Group 144B.
*Thorns.*—Incidence: 1 thorn per 10 cm of stem. Size: Average length: 10 mm. Color: Greyed-Green Group 147A. Shape: Concave.
*Surface.*—Young wood: Smooth. Older wood: Rough.

Plant foliage: Normal number of leaflets on normal leaves in middle of the stem: 5 to 7 leaflets.

*Leaf size.*—160 mm (l)×90 mm (w).

*Quantity.*—1 leaf per every 5 cm on avrage.

*Color.*—Mature Foliage: Upper Leaf Surface: Green Group 137A. Lower Leaf Surface: Yellow-Green Group 146A. Juvenile foliage: Upper Leaf Surface: Yellow-Green Group 144A. Lower Leaf Surface: Yellow-Green Group 146C.

*Anthocyanin intonation.*—Location: Rachis and stipule. Color: Greyed-Red Group 182B.

Plant leaves and leaflets:

*Stipules.*—Size: 25 mm long×8 mm wide. Color: Green Group 137A. Shape: Linear with slightly narrow base and outward extending apecies. Margins: Serrated with stipitate glands along the leaf margin. Anthocyanin: Color: Greyed-Red Group 182B.

*Petiole.*—Length: 20 mm to 25 mm. Diameter: 2 mm. Color: Yellow-Green Group 144A. Underneath: Yellow-Green Group 144B. Stipitate glands observed. Margins: Stipitate glands present. Anthocyanin: Color: Grey-Red Group 182D.

*Rachis.*—Length: 85 mm. Color: Yellow-Green Group 144A. Underneath: Very limited number of stipitate glands present. Margins: Occasional stipitate glands. Anthocyanin: Color: Grey-Purple Group 185D.

*Leaflet.*—Size: 46 mm (l)×40 mm (w). Edge: Serrated. Shape: Broadly ovate. Base: Rounded. Apex: Cuspidate. Texture: Smooth. Appearance: Glossy. Thickness: Leathery. Arrangement: Odd pinnate. Venation: Reticulate.

Disease resistance: Average resistance to mildew, rust, black spot, and Botrytis under normal growing conditions in Jackson County, Oreg.

Cold hardiness: The variety 'POULcs004' has been found to be cold tolerant to USDA plant hardiness zone 7.

It is claimed:

1. A new and distinct variety of rose plant of the Floribunda rose class, substantially as herein illustrated and described as a distinct and novel rose variety due to its abundant White flowers, disease resistance, and extended period of bloom.

* * * * *

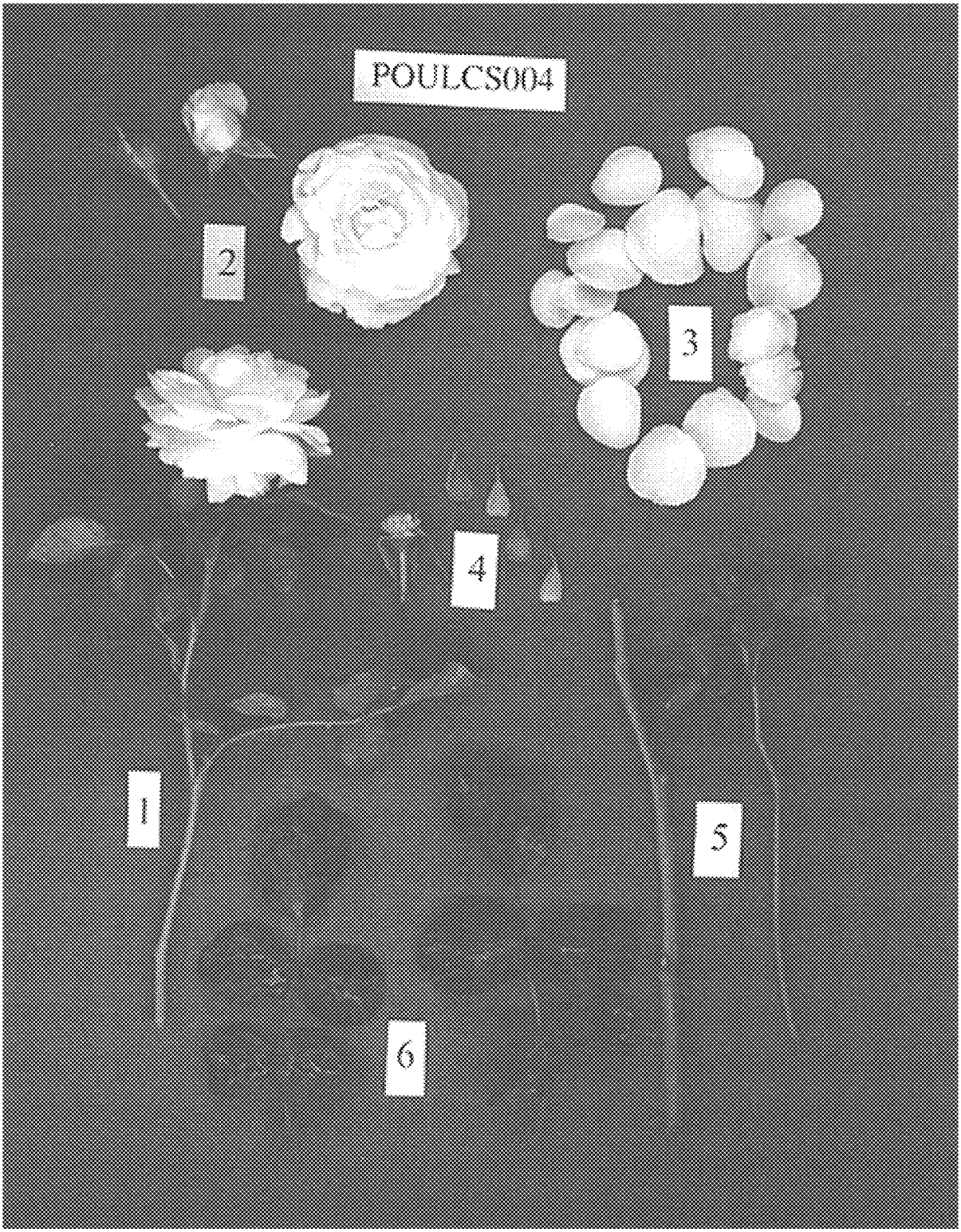
POULCS004
2
3
4
1
5
6